United States Patent [19]

Lyssy

[11] 4,112,739

[45] Sep. 12, 1978

[54] PROCESS AND APPARATUS FOR THE ISOSTATIC MEASUREMENT OF THE PERMEABILITY OF A MATERIAL TO THE PASSAGE THERETHROUGH OF A GAS OR VAPOR

[76] Inventor: Georges H. Lyssy, Rotfluhstrasse 87, CH 8702 Zollikon 2H, Switzerland

[21] Appl. No.: 841,956

[22] Filed: Oct. 13, 1977

[30] Foreign Application Priority Data

May 20, 1977 [CH] Switzerland .............. 006222/75

[51] Int. Cl.$^2$ ............................................. G01N 15/08
[52] U.S. Cl. ............................................. 73/38; 73/49.3
[58] Field of Search ................ 73/38, 40.7, 49.3, 45.4

[56] References Cited

U.S. PATENT DOCUMENTS

| 3,352,146 | 11/1967 | Lyssy | 73/38 |
| 3,572,096 | 3/1971 | Meyer | 73/40.7 |
| 3,926,561 | 12/1975 | Lucero | 73/38 |

*Primary Examiner*—Anthony V. Ciarlante
*Attorney, Agent, or Firm*—Wenderoth, Lind & Ponack

[57] ABSTRACT

A gas-tight chamber has positioned therein a material to be tested such that first and second opposite sides of the material are isolated from each other within the chamber. An enclosed reference circuit includes a first portion of the interior of the chamber which is on the first side of the material. A reference gas is continuously circulated through the reference circuit at the same pressure as the gas or vapor which exists in a second portion of the chamber which is on the second side of the material. This gas or vapor will permeate through the material, from the second side to the first side thereof, into the reference gas within the reference circuit as a function of the permeability of the material. A carrier circuit includes a gas chromatography detection apparatus, and a carrier gas of the same type of gas as the reference gas is continuously passed through the carrier circuit at a pressure higher than the pressure of the reference gas. A portion of the reference circuit is periodically switched to the carrier circuit, thereby injecting into the carrier circuit a portion of the reference gas, contaminated by the gas or vapor, such that the higher pressure carrier gas carries this portion of the contaminated reference gas to the detection apparatus, which then measures the amounts of the components of the gas or vapor in the contaminated reference gas as an indication of the permeability of the material.

17 Claims, 7 Drawing Figures

PROCESS AND APPARATUS FOR THE ISOSTATIC MEASUREMENT OF THE PERMEABILITY OF A MATERIAL TO THE PASSAGE THERETHROUGH OF A GAS OR VAPOR

BACKGROUND OF THE INVENTION

The present invention relates to an apparatus for the isostatic measurement of the permeability of a material to the passage therethrough of a gas or vapor.

More particularly, the present invention is directed to such a process and apparatus which is capable of determining the permeability of a material in sheet or foil form, as well as material in the form of an enclosed or three-dimensional wrapper or container.

U.S. Pat. Nos. 3,301,043 and 3,352,146 disclose systems for measuring the permeability of materials by a manometric process wherein a pressure difference is created between opposite sides of the material. Such systems have the advantage that measurable results are obtained relatively rapidly.

However, while these prior art systems relatively accurately duplicate certain situations, such as wherein bottle or can-type containers contain therein a product, such as beer, maintained under pressure, these systems obviously fail to duplicate actual conditions existing in a great many other types of packaging situations. For example, a great many types of products are wrapped or enclosed within a wrapping material wherein the pressure within the wrapper is the same as the pressure (normally atmospheric) surrounding the wrapper. It will be apparent that the above noted prior art systems, wherein a pressure difference is created across the material, do not test for permeability or leakage of the material under conditions corresponding to actual use of the material.

SUMMARY OF THE INVENTION

Accordingly, a primary object of the present invention is to provide a process and apparatus whereby a material, either in sheet or foil form or in enclosed three-dimensional form, may be tested to determine the permeability thereof to the passage therethrough of gases or vapor, under conditions of isostatic equilibrium.

It is a further object of the present invention to provide such a process and apparatus whereby detection and measurement of permeability is carried out by gas chromatography detection means.

The above objects are achieved in accordance with the present invention by providing a gas-tight chamber within which is positioned a material to be tested, such that first and second opposite sides of the material are isolated from each other within the chamber. When the material to be tested is in sheet or foil form, the sheet or foil may divide the chamber into separate compartments. When the material to be tested is in enclosed, three-dimensional form, such as a wrapper or container, then the wrapper or container may be placed within the chamber. The volume of the chamber exterior of the container represents a first portion of the interior of the chamber, and the volume of the interior of the container represents a second portion of the interior of the chamber. An enclosed reference circuit includes the first portion of the interior of the chamber. A reference gas is supplied from a reference source through the reference circuit so that the first portion of the interior of the chamber is completely flushed of any gas other than the reference gas. When the first portion of the interior of the chamber contains only reference gas, then the reference circuit is isolated from the source of gas, and the reference gas is continually circulated through the reference circuit including the first portion of the interior of the chamber. The reference gas is maintained at the same pressure as the gas or vapor in the second portion of the interior of the chamber. Thus, the opposite sides of the material being tested are maintained in isostatic equilibrium.

As the reference gas circulates through the first portion of the interior of the chamber, the gas or vapor in the second portion of the interior of the chamber will permeate through the material as a function of the permeability of the material. This gas or vapor will then become mixed with the reference gas within the reference circuit, such that the reference gas becomes contaminated thereby.

There is also provided a carrier circuit which includes a conventional gas chromatography detection apparatus. A carrier gas, of the same type as the reference gas, is continuously passed through the carrier circuit. The carrier gas is however maintained at a pressure higher than the pressure of the reference gas. Portions of the reference circuit and carrier circuit are arranged such that a specific portion of the reference circuit may be selectively switched to the carrier circuit, whereby a portion of the contaminated reference gas may be instantaneously injected into the carrier circuit. The relatively higher pressure carrier gas within the carrier circuit then carries this injected gas to the gas chromatography detection apparatus which then detects and measures the quantities of components of the contaminating gas or vapor, as an indication of the permeability of the material.

In a preferred arrangement of the present invention, both the reference gas and carrier gas are supplied from a single pressurized gas source, and the desired respective pressures of the reference gas and carrier gas are achieved by separate pressure reducers.

The reference gas and carrier gas may be any gas which would be suitable for achieving the functions discussed above. In the present application reference is made to helium, however it is to be understood that other gases might be used.

It will be apparent that leakage of the gas or vapor through the material being tested under isostatic conditions will be very slight. Therefore, it is extremely important that the system be designed such that minor leakages into the system which are virtually unavoidable do not contaminate the test and thereby render inaccurate the test results. In accordance with the present invention such contamination is avoided by enclosing those portions of the system which are susceptible to leakage within a housing which has therein a small gas outlet. The carrier gas is discharged from the carrier circuit into the interior of the housing, such that the entire interior of the housing is continuously flushed with the carrier gas. Specifically, all valves, connections and the gas chromatography detection apparatus are enclosed within the housing. Therefore, if any leakage occurs through such valves, connections, etc. into the reference circuit or the carrier circuit, then such leakage will be of the same gas which is being passed through such circuits.

It is specifically to be understood that the actual structure and arrangement of the gas chromatography detection apparatus does not in and of itself form a portion of the present invention. Rather, the present invention is designed to be adaptable to any conventional gas chromatography detection apparatus.

BRIEF DESCRIPTION OF THE DRAWINGS

Other objects, features and advantages of the present invention will become apparent from the following detailed description of preferred embodiments thereof, taken in conjunction with the accompanying drawings, wherein.

DETAILED DESCRIPTION OF THE INVENTION

Figure 1A:
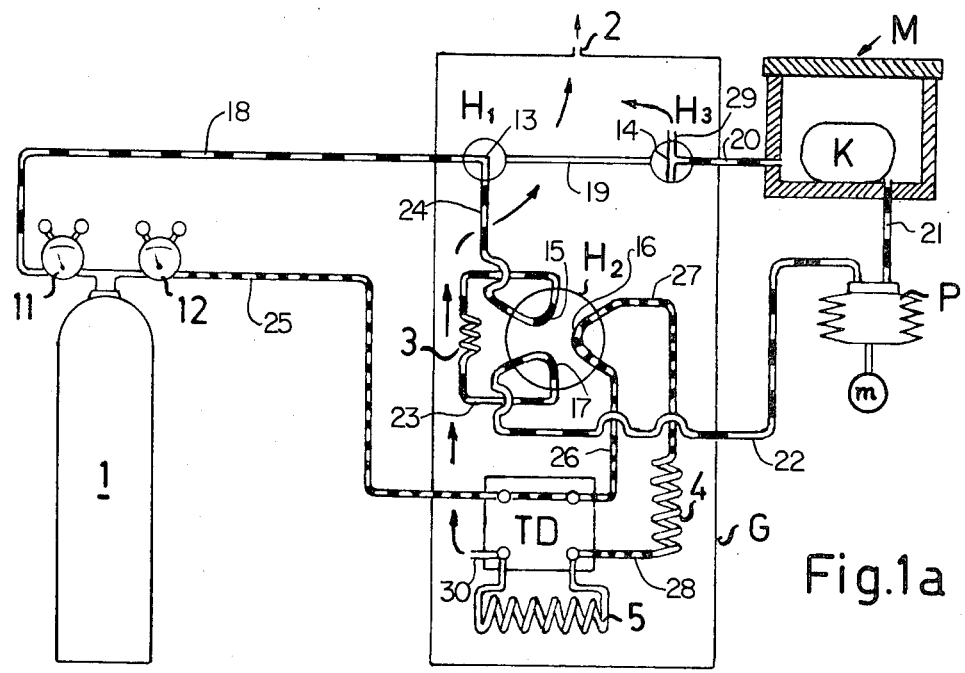
FIG. 1a is a schematic diagram illustrating one embodiment of an apparatus according to the present invention and for use in carrying out the process of the present invention, the apparatus being shown in a preliminary, flushing stage.
Figure 1B:
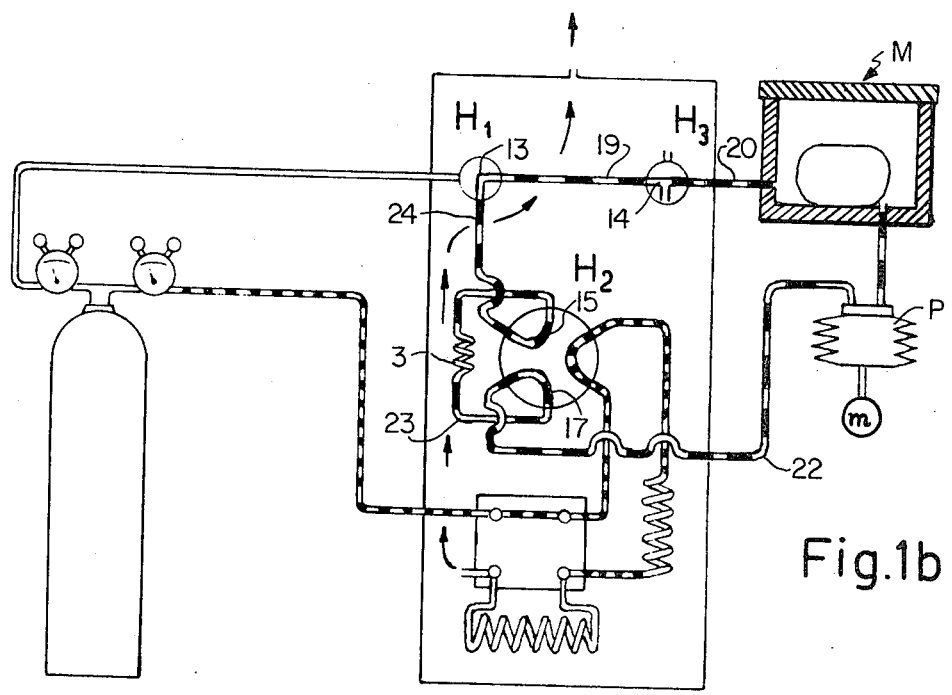
FIG. 1b is a view similar to FIG. 1a, but showing the apparatus in an operational, circulating stage.
Figure 1C:
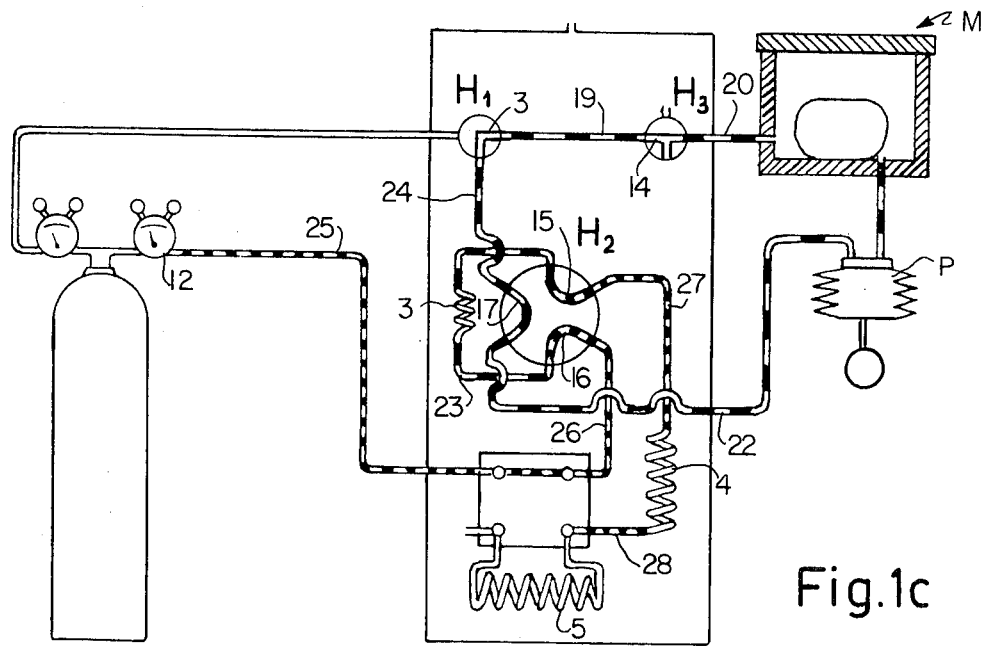
FIG. 1c is a view similar to FIGS. 1a and 1b, but showing the apparatus in a measuring, injecting stage.

With reference now to FIGS. 1a-1c of the drawings, the apparatus of the present invention includes a source 1 of reference and carrier gas. In the illustrated arrangement, the source 1 comprises a gas cylinder containing pressurized gas, for example helium. The apparatus further includes a substantially enclosed housing G, a pump P operated by a motor m, and a gas-tight, enclosed measuring or testing chamber M. The pump P may comprise a diaphragm pump. It is important in accordance with the present invention that the pump P be absolutely gas-tight such that no exterior contaminating gas may leak into pump P. Diaphragm pumps having this characteristic have been developed for the space program and are commercially available.

The outlet of gas cylinder source 1 is provided with reducing valves 11 and 12. One of the reducing valves, i.e. valve 11, is adapted to reduce the pressure of the gas within the gas cylinder to a specific first pressure equal to the pressure existing within an enclosed and wrapped sample K which is positioned within measuring chamber M. For instance, sample K may be a food product, for example a block of cheese, which is enclosed by a wrapping material or container which is intended to be gas-tight. The reducing valve 11 is adapted to reduce the pressure of the gas within source 1 to the same pressure as normally existing within the wrapping or container of sample K. Normally, it would be expected that the pressure within the wrapping or container of sample K would be atmospheric pressure, and therefore reducing valve 11 would be adapted to reduce the pressure of the gas within source 1 to atmospheric pressure, i.e. one atmosphere of pressure.

Reducing valve 12 on the other hand, is adapted to reduce the pressure within gas source 1 to a second pressure which is greater than the pressure existing within the wrapping or container of sample K. For purposes of this description, it will be assumed that reducing valve 12 reduces the pressure of the gas within gas source 1 to a pressure of four atmospheres.

Entirely enclosed within housing G are three cocks or valves $H_1$, $H_2$ and $H_3$, as well as a conventional chromatography apparatus. This chromatography apparatus may include a conventional thermal detector TD, first coil 4 and second coil 5. This chromatography apparatus may also include a conventional recording apparatus operatively connected in a known manner to thermal detector TD. These elements are entirely conventional and would be readily understood by one ordinarily skilled in the gas chromatography art. Accordingly, the recording apparatus is not shown, and the other chromatography apparatus elements are only schematically shown. Further, these elements are not discussed in further substantial detail, inasmuch as it is intended that any conventional and commercially available chromatography apparatus operating on the basis of thermal detection may be employed in the present invention.

Cock $H_1$ has therein a single passage, for example an L-shaped passage 13. Cock $H_3$ has therein a T-shaped passage 14. Cock $H_2$ has therein three passages 15, 16 and 17.

The apparatus of the present invention further includes conduit 18 extending between reducing valve 11 and cock $H_1$, conduit 19 extending between cock $H_1$ and cock $H_3$, conduit 20 extending from cock $H_3$ into the interior of measuring chamber M, conduit 21 extending from the interior of measuring chamber M to the outlet of pump P, conduit 22 extending from the inlet of pump P to cock $H_2$, conduit 23, which includes a sample coil 3, extending from a first position at cock $H_2$ to a second position at cock $H_2$, conduit 24 extending from cock $H_2$ to cock $H_1$, conduit 25 extending from reducing valve 12 into housing G and to the thermal detector TD of the gas chromatography apparatus, conduit 26 extending from the thermal detector TD to cock $H_2$, conduit 27 extending from cock $H_2$ to first coil 4, and conduit 28 extending from first coil 4 to second coil 5.

When the apparatus of the present invention is to be put into operation, cocks $H_1$, $H_2$ and $H_3$ are placed in the positions indicated in FIG. 1a of the drawings, a sample K is placed within measuring chamber M, reducing valves 11 and 12 are opened, and pump P is operated. Pressurized gas, such as helium, exiting from source 1 passes through reducing valve 11 which reduces the pressure of the gas to the pressure of the gas or atmosphere within the wrapping or container of sample K, for example to atmospheric pressure. This gas is passed through conduit 18, passage 13 of cock $H_1$, conduit 24, passage 15 of cock $H_2$, conduit 23 including sample coil 3, conduit 17 of cock $H_2$, conduit 22, pump P, conduit 21, the interior of measuring chamber M, conduit 20, passage 14 of cock $H_3$, and through outlet 29 of cock $H_3$ into the interior of housing G. This gas, i.e. helium, exits from the interior of housing G through opening 2. Thus, the helium gas supplied through reducing valve 11 operates to flush the system, and specifically the interior of measuring chamber M, until the interior of measuring chamber M is entirely filled with the helium gas. This helium gas thus acts as a reference gas.

Simultaneous with the above flushing operation, helium gas passes from source 1 through reducing valve 12 at an elevated pressure, for example four atmospheres as mentioned above. The helium gas which exits through reducing valve 12 operates as a chromatography carrier gas and passes through conduit 25, thermal detector TD of the gas chromatography apparatus, conduit 26, passage 16 of cock $H_2$, conduit 27, first coil 4, conduit 28, second coil 5, and outlet 30 into the interior of housing G. This portion of the helium gas also continually exits from the interior of housing G through opening 2.

The flushing operation illustrated in FIG. 1a is continued until all air or other gas within the interior of measuring chamber M is replaced by the reference gas, i.e. helium, and at such time the system is changed to the circulating stage illustrated in FIG. 1b of the drawings. Specifically, cock $H_1$ is rotated such that passage 13 thereof connects conduits 19 and 24, and cock $H_3$ is rotated such that passage 14 thereof connects conduits 19 and 20. Thus, conduit 18 and reducing valve 11 are cut off from the circuit, and the reference helium gas is prevented from escaping through outlet 29 into the interior of housing G. Accordingly, there is formed a completely enclosed and endless circulating path from pump P through conduit 21, the interior of measuring chamber M, conduit 20, passage 14 of cock $H_3$, conduit 19, passage 13 of cock $H_1$, conduit 24, passage 15 of cock $H_2$, conduit 23 including sample coil 3, passage 17 of cock $H_2$ and conduit 22 returning to pump P.

During the operation of this closed circuit wherein reference helium gas is continually pumped through the interior of measuring chamber M, helium carrier gas at an elevated pressure continues to be forced through the circuit including the gas chromatography apparatus as mentioned above such that helium gas continues to be expelled through outlet 30 into the interior of housing G. Thus, the interior of housing G is still continually flushed with helium gas. Accordingly, even if cocks $H_1$, $H_2$ and $H_3$ are not entirely gas-tight, there is no danger of contaminating gas entering into the cocks, since the cocks are entirely surrounded by the helium carrier gas. However, since the carrier gas is identical to the reference gas, even if the carrier gas surrounding the cocks leaks into the cocks, the reference gas will not be contaminated.

During normal operation, the apparatus is operated in the position and stage illustrated in FIG. 1b of the drawings. During such operation, if the wrapping or container of sample K is permeable to the passage therethrough of the gas or air contained therein, then during the recirculation of the reference helium gas through the interior of measuring chamber M, such reference gas will gradually become contaminated by such interior gas or air permeating through the container or wrapping of sample K. At selected intervals, for example once every hour, cock $H_2$ is moved from the position shown in FIGS. 1a and 1b to the position shown in FIG. 1c. Cock $H_2$ is maintained at the position shown in FIG. 1c for only a short period of time, for example from 10 to 15 seconds, and is then returned to the normal position shown in FIG. 1b.

When cock $H_2$ is moved to the position of FIG. 1c, then the recirculating reference circuit is altered to exclude the sample coil 3. That is, reference circuit now passes from pump P, through the interior of measuring chamber M, conduit 20, passage 14 of cock $H_3$, conduit 19, passage 13 of cock $H_1$, conduit 24, passage 17 of cock $H_2$, and conduit 22 back to pump P.

Furthermore, conduit 23, which includes sample coil 3, and which had previously been a portion of the reference circuit, is now switched to the carrier circuit of the gas chromatography apparatus. That is, in the position shown in FIG. 1c, helium carrier gas exits from reducing valve 12, through conduit 25, conduit 26, and passage 16 of cock $H_2$ into conduit 23. Thus, the pressure of this carrier gas forces the gas within sample coil 3 (and this gas contains the helium reference gas "contaminated" by gas which permeated from the interior of sample K through the wrapping or container thereof into the reference circuit) through passage 15 of cock $H_2$, conduit 27, coil 4, conduit 28, and coil 5.

Figure 4:
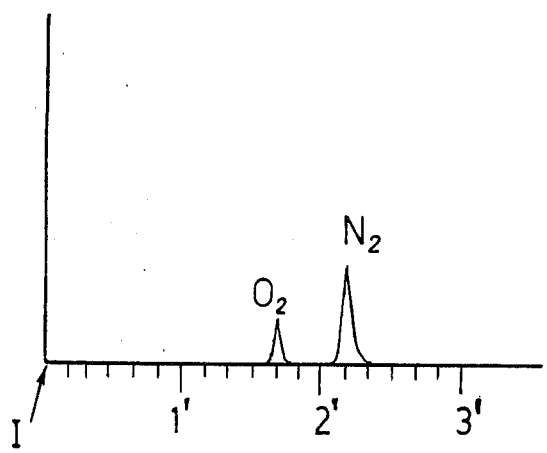
FIG. 4 is a graph illustrating a chromatography recording employed in initially calibrating the apparatus of the invention.

As mentioned previously, the specific construction of the gas chromatography apparatus is intended to be conventional. Such conventional apparatus would include absorption materials within coils 4 and 5. As stated above, the gas within sample coil 3 was previously in the reference circuit but is now injected into the carrier circuit. This gas within sample coil 3 contains contaminating gas components which permeated into the reference circuit through the wrapping or container of the sample K. These various contaminating gas components slowly traverse coils 4 and 5. However, as is known in the gas chromatography art, the different contaminating gas components will require different lengths of time to traverse coils 4 and 5. Such time difference allows the presence of the various contaminating gas components to be detected by the thermal detector of the gas chromatography apparatus and for such detection to be recorded, for example as graphically illustrated in FIGS. 4 and 5, to be discussed in more detail below.

After a measurement and detection is made, in the manner discussed above with reference to FIG. 1c, cock $H_2$ is returned to the position shown in FIG. 1b of the drawings, at which time the reference circuit including sample coil 3 will initially be filled only with helium reference gas. As the circulation of the reference circuit thereafter continues, the reference gas will again be gradually contaminated by gas from the interior of sample K permeating through the wrapper or container thereof into the interior of measuring chamber M. At desired and predetermined time intervals thereafter, cock $H_2$ may be switched for short periods of time to the position shown in FIG. 1c, such that other contaminated gas samples existing in sample coil 3 may be injected into the carrier circuit and detected and measured by the gas chromatography apparatus.

Figures 2, 3:
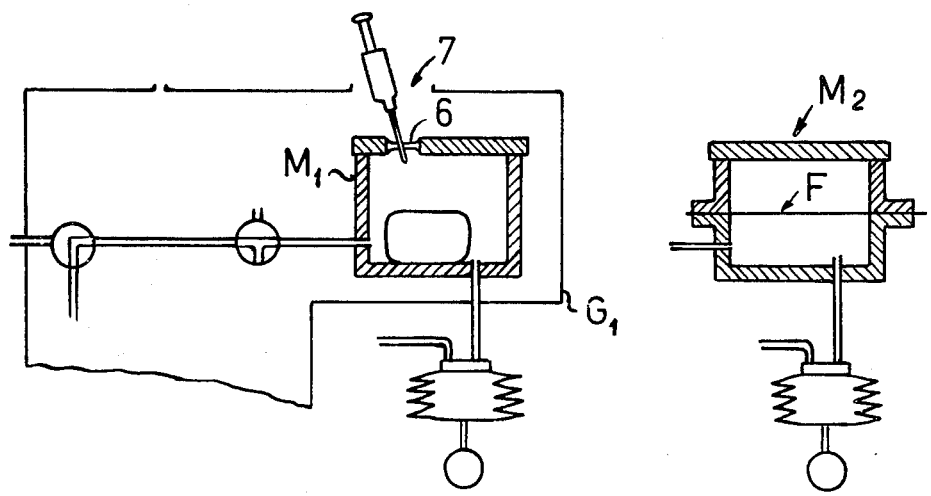
FIG. 2 is a partial diagrammatic view illustrating a modification of the apparatus of FIGS. 1a-1c.
FIG. 3 is a partial view of a further modification of the apparatus of the invention, and specifically wherein the measuring or sample chamber is modified to test the permeability of a sheet or foil.

The apparatus of the present invention may be modified as shown in FIG. 2 to allow for calibration of the gas chromatography apparatus, and specifically the recorder thereof. For example, the measuring chamber $M_1$ may include therein a pierceable diaphragm 6 such that a known quantity of a known gas may be injected into the interior of the measuring chamber. Since pierced diaphragm 6 represents a source of possible leakage into the system, it is preferable that the housing $G_1$ also completely enclose the measuring chamber $M_1$, as shown in FIG. 2. Therefore, even if gas is to leak into the interior of chamber $M_1$, such gas will be only helium which continuously circulates within the interior of the housing.

In calibrating the apparatus, the entire apparatus would be flushed for a considerable length of time, for example 24 hours, as shown in FIG. 1a. The apparatus would then be brought to the condition shown in FIG. 1b, and a known quantity of a known reference gas, for example 1 cc of air, would be injected through diaphragm 6 into the interior of the measuring chamber as shown in FIG. 2. Thus, the reference circuit would have circulating therein a known quantity of a known contaminating gas. After a relatively short period of circulation of the reference circuit, cock $H_2$ would be shifted for a short period of time to the condition shown in FIG. 1c, so that the content of sample coil 3 would be injected into the carrier circuit. Thus, the reference gas, "contaminated" to a known extent by the known contaminant gas would pass through the gas chromatography apparatus and be detected thereby. The recorder of the gas chromatography apparatus would render a recording similar to that shown in FIG. 4 when the known contaminating gas is air. That is, the injection, or switching from the condition of FIG. 1b to the condition of FIG. 1c, would take place at point I. After approximately 1¾ minutes, the oxygen contained in the contaminating air is recorded, and the nitrogen therein is recorded after approximately two minutes. This is in accordance with known gas chromatography detection and recording practice. The areas encompassed within the respective oxygen and nitrogen curves represent proportional existing quantities of the respective contaminants. For example, in FIG. 4 of the drawings the contaminant air contains approximately four times as much nitrogen as oxygen. If the measuring chamber and the various associated conduits and passages have a volume of approximately 1,000 cc, the areas of the oxygen and nitrogen recordings in FIG. 4 would represent a contamination of approximately 1 ppm.

By the above procedure, it would be possible to calibrate a given apparatus to be able to determine quantities of given contaminants detected in the manner described above by the gas chromatography apparatus.

Figure 5:
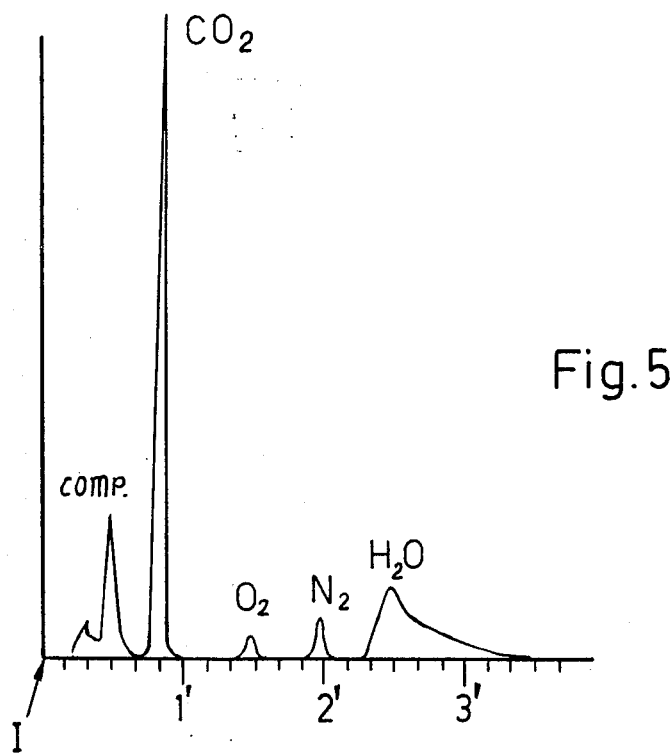
FIG. 5 is a graph illustrating an actual chromatography recording resulting from employing the apparatus of the invention.

FIG. 5 represents an actual measurement made employing the apparatus illustrated in FIGS. 1a–1c, wherein the sample K was a block of cheese wrapped in a material the permeability of which was measured employing the apparatus and process of the invention.

The above description has been made with reference to testing the permeability of a wrapping or container of a three-dimensional configuration, i.e. surrounding or adapted to surround a product. However, it is to be understood that the present invention is equally applicable for detecting and measuring the permeability of sheet material to the passage therethrough of a gas. Specifically, and with reference to FIG. 3 of the drawings, a measuring chamber $M_2$ is divided into two chambers by a sheet or foil of material F. The lower chamber shown in FIG. 3 corresponds to the interior of the measuring chamber M illustrated in FIGS. 1a–1c and comprises a portion of the above described circulating reference circuit. The upper chamber, i.e. the chamber above sheet F in FIG. 3, corresponds to the interior of the sample K illustrated in FIGS. 1a–1c. The apparatus is in all other respects identical with the apparatus illustrated and described with reference to FIGS. 1a–1c, and the process is identical with that described above. In carrying out the process of the present invention for detecting and measuring the permeability of sheet F, a measurement is made of the permeability of sheet F to the passage therethrough of the gas contained in the upper chamber shown in FIG. 3.

It is to be understood that in accordance with the present invention, the system is first flushed as shown in FIG. 1a. The system is then switched to the circulating stage illustrated in FIG. 1b, and periodically the system is switched to the condition illustrated in FIG. 1c whereby gas samples are injected into the carrier circuit and detected and measured by the gas chromatography apparatus. In actual practice, it may be expected that during the initial measurements, little contamination will be detected, unless the material being tested is extremely permeable. However, after several samples, the gas chromatography apparatus will detect and record contamination in a manner such that both qualitative and quantitative evaluation will be possible. For example, the actual recording shown in FIG. 5 was taken after 65 hours.

It is advantageous in accordance with the present invention for the dead volume of injection cock $H_2$ to be so large that the carrier gas contained therein and subjected to the higher pressure allowed by reducing valve 12 corresponds to the volume within conduit 23 which includes sample coil 3, after being expanded to the pressure of the reference circuit. Therefore, when the system is switched from the condition shown in FIG. 1c back to the condition shown in FIG. 1b, the gas within the dead volume of cock $H_2$ is expanded within conduit 23 such that there is no change in pressure within the reference circuit.

Again, it is to be understood that the exact structure and configuration of the gas chromatography apparatus in and of itself forms no portion of the present invention. Rather, the concept of the present invention involves the adaptation and use of any known and commercially available gas chromatography apparatus into the novel apparatus and process described above. Conventionally, the thermal detector TD of the gas chromatography apparatus includes hot wires arranged in a bridge circuit, such that variation in the resistance due to cooling by different gases of different conductivity is measured and then recorded. However, it is believed to be apparent that the process and apparatus of the present invention is adaptable to other types of conventional gas chromatography apparatus.

Although specific preferred embodiments of the present invention have been described and illustrated, it is to be understood that various modifications may be made to the above specifically described structural arrangements and process operations without departing from the scope of the present invention. Specifically, the arrangement of the conduits and valves or cocks shown in FIGS. 1a–1c can be changed or replaced to include other specific structural features. The important feature of the present invention is that there be an enclosed reference circuit which circulates a reference gas over or across the material being tested, that there be a carrier circuit including the gas chromatography detection apparatus which has passing therethrough a carrier gas identical to the reference gas but at a higher pressure, and that a portion of the reference circuit may be switched to the carrier circuit such that a portion of the contaminated reference gas may be instantaneously injected into the carrier circuit.

What is claimed is:

1. A process for the isostatic measurement of the permeability of a material to the passage therethrough of gas or vapor, said process comprising:
   positioning a material to be tested within a gas-tight chamber such that first and second opposite sides of said material are isolated from each other within said chamber;
   circulating a reference gas through an enclosed reference circuit which includes a first portion of the interior of said chamber which is on said first side of said material;

maintaining the pressure of said reference gas within said reference circuit at the same pressure as the gas or vapor existing in a second portion of said chamber which is on said second side of said material;

whereby said gas or vapor will permeate through said material, from said second side to said first side thereof, into said reference gas within said reference circuit, as a function of the permeability of said material, thereby forming contaminated reference gas;

continuously passing, as a carrier gas, the same type of gas as said reference gas through a carrier circuit which includes a gas chromatography detection apparatus;

maintaining said carrier gas at a pressure higher than said pressure of said reference gas;

periodically injecting a portion of said contaminated reference gas within said reference circuit into said carrier circuit, whereby said carrier gas carries said portion of said contaminated reference gas to said detection apparatus; and measuring the amounts of the components of said gas or vapor in said contaminated reference gas, by operation of said detection apparatus, as an indication of the permeability of said material.

2. A process as claimed in claim 1, wherein said reference gas and said gas are supplied from the same gas source.

3. A process as claimed in claim 1, wherein said reference gas and said carrier gas are helium.

4. A process as claimed in claim 1, wherein said material comprises a sheet which is positioned to divide said chamber into two separate compartments.

5. A process as claimed in claim 1, wherein said material comprises an enclosed three-dimensional container which is positioned within said chamber.

6. A process as claimed in claim 1, further comprising, after said step of injecting, returning from said carrier circuit to said reference circuit an amount of reference gas equal in amount to that injected from said reference circuit into said carrier circuit.

7. A process as claimed in claim 1, further comprising calibrating said detection apparatus by injecting a known quantity of a known gas into said reference circuit.

8. A process as claimed in claim 1, further comprising, prior to said step of circulating, flushing out said first portion of the interior of said chamber by continuously passing fresh reference gas therethrough until said first portion contains therein only said reference gas.

9. An apparatus for the isostatic measurement of the permeability of a material to the passage therethrough of a gas or vapor, said apparatus comprising:

a gas-tight chamber adapted to have positioned therein a material to be tested such that first and second opposite sides of said material are isolated from each other within said chamber;

an enclosed reference circuit including a first portion of the interior of said chamber which is on said first side of said material;

means for continuously circulating through said reference circuit a reference gas at the same pressure as the gas or vapor existing in a second portion of said chamber which is on said second side of said material, such that said gas or vapor will permeate through said material, from said second side to said first side thereof, into said reference gas within said reference circuit as a function of the permeability of said material, thus forming contaminated reference gas;

a carrier circuit including a gas chromatography detection apparatus;

means for continuously passing, as a carrier gas, the same type of gas as said reference gas, but at a pressure higher than said pressure of said reference gas, through said carrier circuit; and means for periodically switching a portion of said reference circuit to said carrier circuit, and for thereby injecting a portion of said contaminated reference gas into said carrier circuit, such that said carrier gas carries said portion of said contaminated reference gas to said detection apparatus which measures amounts of the components of said gas or vapor in said contaminated reference gas as an indication of the permeability of said material.

10. An apparatus as claimed in claim 9, wherein said reference gas and said carrier gas are helium.

11. An apparatus as claimed in claim 9, wherein said material comprises a sheet which is positioned to divide said chamber into two separate compartments.

12. An apparatus as claimed in claim 9, wherein said material comprises an enclosed three-dimensional container which is positioned within said chamber.

13. An apparatus as claimed in claim 9, wherein said circulating means comprises a pressurized reference gas source, means for reducing the pressure of said reference gas in said source to said pressure of said gas or vapor, and pump means for pumping said reference gas through said reference circuit.

14. An apparatus as claimed in claim 13, wherein said carrier gas is supplied from said source, and said passing means comprises a pressure regulator for supplying said gas from said source to said carrier circuit.

15. An apparatus as claimed in claim 9, further comprising a housing enclosing said detection apparatus, said carrier circuit opening into the interior of said housing, said housing having a gas outlet, such that said carrier gas is continuously discharged into the interior of said housing and said housing is continuously flushed by said carrier gas.

16. An apparatus as claimed in claim 15, wherein said switching means comprises a valve positioned within said housing, said valve having therein plural passage means, said valve having a first position whereat said portion of said reference circuit communicates through first passage means of said valve with the remainder of said reference circuit, and said valve having a second position whereat said portion of said reference circuit communicates through second passage means of said valve with said carrier circuit.

17. An apparatus as claimed in claim 15, wherein said chamber is provided with a pierceable diaphragm, and said chamber is positioned within said housing.

* * * * *